United States Patent [19]

Kitahata et al.

[11] Patent Number: 5,529,927
[45] Date of Patent: Jun. 25, 1996

[54] "ALGA SPECIES LOBSPHAERA TM-33 (ATCC 75630) WHICH IS USEFUL FOR PREPARING TREHALASE"

[75] Inventors: Sumio Kitahata; Hirofumi Nakano; Tsutomu Washino; Masamitsu Moriwaki, all of Osaka, Japan

[73] Assignee: San-Ei Gen F.F.I., Inc., Osaka, Japan

[21] Appl. No.: 231,318

[22] Filed: Apr. 22, 1994

[30] Foreign Application Priority Data

Dec. 28, 1993 [JP] Japan ................... 5-350260

[51] Int. Cl.$^6$ .................................. C12N 1/12
[52] U.S. Cl. ................. 435/257.1; 435/100; 435/200; 435/257.3; 435/946
[58] Field of Search .................. 435/257.1, 257.3, 435/946, 100, 200

[56] References Cited

FOREIGN PATENT DOCUMENTS

| 22917/1985 | 6/1985 | Japan . |
| 149972/1985 | 8/1985 | Japan . |
| 174094/1987 | 7/1987 | Japan . |
| 240758/1988 | 10/1988 | Japan . |
| 60998/1988 | 11/1988 | Japan . |
| 211882/1993 | 8/1993 | Japan . |
| WO89/00012 | 1/1989 | WIPO . |

OTHER PUBLICATIONS

Methods in Enzymology, (1972) 23, pp. 996–1000.
J. Bacteriol., (1968) vol. 96, pp. 106–110.
J. Biol. Chem., (1964) vol. 239, pp. 1671–1673.
J. Bacteriol., (1966) vol. 91, pp. 1883–1887.
J. Bacteriol., (1973) vol. 115, pp. 582–591.
Biochim. Biophys. Acta, 525 (1978), pp. 162–170.
Biochim. Biophys. Acta 391 (1975), pp. 154–161.
Can. J. Microbiol., (1978) vol. 24, pp. 1280–1283.
J. Am. Chem. Soc., (1950) pp. 2059–1061.
Nippon Nogei Kagaku Kaishi, vol. 27, (1953) pp. 412–416.
Nouveau Journal de Chimie, (1980) vol. 4. pp. 59–68.
Biochimica et Biophysica Acta, (1984) 803, pp. 284–289.
Biochimica et Biophysica Acta, (1969) 184, pp. 77–82.
"Chlorophyceae," Dr. J. Komarek & Dr. B. Fott, Huber–Pestalozzi(ed.) (1983).
J. Biol. Chem., (1994) 153, pp. 375–380.
Acta Chem. Scand., (1966) 20, pp. 820–834.
Anal. Biochem., (1969) 30, pp. 148–152.
Acta Chem. Scand., (1966) 20, p. 820–834.
Anal. Biochem., (1969) 30, pp. 148–152.

Primary Examiner—Herbert J. Lilling
Attorney, Agent, or Firm—Bryan Cave

[57] ABSTRACT

Novel trehalase having the properties that it hydrolyzes $\alpha,\alpha'$-trehalose, 2,2'-dideoxy-$\alpha,\alpha'$-trehalose and 2-deoxy-$\alpha,\alpha'$-trehalose into the respective constituting sugars while it does not act on neotrehalose, lactose, maltose, celobiose and sucrose; its optimum pH is 5 to 6; its optimum temperature is 65° C.; it is stable against heating up to 65° C.; its molecular weight as measured by a gel filtration is 400,000 to 500,000 while the molecular weight of the subunit as measured by a sodium dodecylsulfate—polyacrylamide gel electrophoresis is 180,000 to 250,000; its isoelectric point as measured by an isoelectricfocusing is 2.7; and it is a glycoprotein.

1 Claim, 11 Drawing Sheets 2,2'-Dideoxytrehalose

Retention Time (min.)

2-Deoxytrehalose

"ALGA SPECIES LOBSPHAERA TM-33 (ATCC 75630) WHICH IS USEFUL FOR PREPARING TREHALASE"

BACKGROUND OF THE INVENTION

1. Field of the Invention

The present invention relates to novel enzyme of trehalase and also to a method of manufacturing sugars by the enzyme. More particularly, it relates to a novel trehalase derived from an alga which belongs to Lobosphaera, Chlorellaceae and also to a method of manufacturing trehalose, 2,2'-dideoxy-$\alpha,\alpha'$-trehalose (hereinafter referred to as 2,2'-dideoxytrehalose) and 2-deoxy-$\alpha,\alpha'$-trehalose (hereinafter referred to as 2-deoxytrehalose) by the enzyme.

2. Description of the Related Art

Trehalose is a kind of nonreducing disaccharide in which two molecules of D-glucose are bonded with the $\alpha,\alpha'$-1,1' linkage. In insects, it is available in their blood and lymph and serves as a stored blood sugar for a mobile energy source. Also, it is said that trehalose exhibits an effect as an antifreezer and hence, insects control in some seasons, its concentration for achieving a resistance against coldness.

Trehalase is an enzyme which hydrolyzes trehalose into two glucose molecules. This enzyme may be found in higher animals (small intestine of rats, pigs, etc.), insects (silkworm, etc.), microorganisms and the like. Various microorganisms are known to produce trehalase, including bacteria such as the Mycobacterium genus (Methods in Enzymology, (1972) 28, 996) or the Streptomyces genus (J. Bacteriol. (1968) 96, 105); yeasts such as the Saccharomyces genus (J. Biol. Chem., (1964) 239, 1671); and filamentous fungi such as the Aspergillus genus (J. Bacteriol., (1966) 91, 1883), the Neurospora genus (J. Bacteriol., (1973) 115, 582), Humicola (Biochim. Biophys. Acta, (1978) 525, 162) or Phycomyces (Biochim. Biophys. Acta, (1975), 391, 154); and the like. All of those contain trehalase either in cells or in spores. Besides the above, the Trichoderma genus (Can. J. Microbiol., (1978) 24, 1280) and the Chaetomium genus (Examined Japanese Patent Publication 22917/85) have been reported as microorganisms producing trehalase outside the cells. However, there has been no report of trehalase derived from Chlorophyceae (green algae).

With regard to the use of trehalose, applications as a sweetening agent causing little dental caries, as an agent action against dental caries, as a prometer on the promulgation of Bifidus bacteria, and as a novel material for food have been proposed (Japanese Laid Open Publication 63/240758). In addition, there is a report that, when a certain amount of trehalose is added to beverages or food materials containing water, denaturation of protein in beverages and food material can be prevented (National Publication of International Application 02/503864). Further, in the field of pharmaceuticals, there is it has been reported that trehalose may be pulled as a, protected agent for protein to inhibit a decrease in enzymatic activity, thereby permitting a storage of the enzyme-labelled antibody for long periods (Japanese Laid Open Publication 60/149972). Moreover, it has also been reported that trehalose is useful for improving the stability of cells upon storage, for stabilizing vaccines and for making trihalose derivatives useful as anticancer agents (Japanese Laid Open Publication 62/174094). For example, it has been known that 2-deoxyglucose inhibits the chain formation of glycoproteins and glycolipids as a metabolic antagonist for glucose and mannose V whereby growth of fibroblast is inhibited and anticancer action results.

In manufacturing trehalose, it is known that trehalose may be produced in vitro by means of an enzymatic reaction, or by method in which trehalose is accumulated in and outside the cells of microorganisms. With regard to the production of trehalose from microorganisms, a method of preparing same from baker's yeast containing large quantity of trehalose is known. For example, a method in which a compressed yeast is extracted with 95% (v/v) ethanol to give trehalose (J. Am. Chem. Soc., (1950) 2059) and one in which baker's yeast is extracted with 90% (v/v) ethanol to give trehalose (Nippon Nogei Kagaku Kaishi, vol. 27, (1953) 412) are known. With regard to an enzymatic method, a method in which maltose is treated with maltose phosphorylase and trehalose phosphorylase to manufacture trehalose has been reported (Examined Japanese Publication 60998/88).

With regard to methods for manufacturing 2,2'-dideoxytrehalose and 2-deoxytrehalose, a method by chemical synthesis (Nouveau Journal De Chimie, (1980) 4, 59) and a method by utilizing metabolism of enzymes (Biochimica et Biophysica Acta, (1984) 803, 284 and Biochimica et Biophysica Acta, (1969) 184, 77) have been described.

However, in the above-mentioned trehalase which is known or is commercially available, there are disadvantages that units produced by the microorganism are low and that the efficiency in the condensation reaction (reverse reaction) from glucose to trehalose is extremely low.

Especially in a method of preparing trehalose by extraction of baker's yeast, a large amount of an organic solvent is necessary and, in addition, complicated steps are necessary for removing the contaminants. In a method of manufacturing trehalose by treating maltose with maltose phosphorylase and trehalose phosphorylase which is a well-known method utilizing enzymes, there are so many disadvantages that the manufacturing steps are complicated and that the manufacture of the enzymes—maltose phosphorylase and trehalose phosphorylase—requires high cost and many difficulties.

There is another method in which trehalose excreted from cells is purified (Japanese Laid Open Publication 05/211882). However, in any of those methods, the manufacturing cost is high and, accordingly, the use is limited.

In a method of manufacturing 2,2'-dideoxytrehalose and 2-deoxytrehalose by means of chemical synthesis, there are disadvantages that the steps are complicated and the yield is low, while in a method by means of metabolism of enzymes, there are disadvantages that the production is low and the purifying steps are complicated.

SUMMARY OF THE INVENTION

In order to solve the above-mentioned problems, the present inventors have widely carried out the search for finding microorganisms producing trehalase in nature and found that a new strain which is considered to belong to a green alga of Lobosphaera, Chlorellaceae, Chlorophyceae, Chlorophyta as a potent producer of a trehalase which meets with the requirements. It has been further found that the resulting enzyme exhibits higher thermal stability than the trehalases which have been reported previously.

The trehalase of the present invention is produced by a green algae of Lobosphaera, Chlorellaceae, Chlorophyceae, Chlorophyta and can be obtained from its culture broth and it has the following characteristic properties: (1) it hydrolyzes $\alpha,\alpha'$-trehalose, 2,2'-dideoxy-$\alpha,\alpha'$-trehalose and 2-deoxy-$\alpha,\alpha'$-trehalose into each of their constituting sugars while it does not act on neotrehalose, lactose, maltose, cellobiose and sucrose; (2) its optimum pH is 5 to 6; (3) its optimum temperature is 65° C.; (4) it is stable against heating up to 65° C.; (5) its molecular weight measured by gel filtration is 400,000–500,000 and the molecular weight of the subunit by sodium dodecylsulfate—polyacrylamide gel electrophoresis (hereinafter referred to as SDS-PAGE) is 180,000–250,000; (6) its isoelectric point measured by isoelectricfocusing is 2.7; and (7) it is a glycoprotein.

DESCRIPTION OF THE DRAWINGS

Drawings attached hereto are as follows.

DETAILED DESCRIPTION OF THE PREDERRED EMBODIMENT

Since the alga collected from the soil in Yao City, Osaka Prefecture exhibited the following morphological and culturing properties, the present inventors tried to identify it by comparing with the algae (stored strains) of various species of Chlorellaceae by referring to Komarek, J. and Fott, B.: Chlorophyceae. In Huber—Pestalozzi (ed.) (1983) 1044, etc. As a result, the alga is similar to Lobosphaera tirolensis but is not exactly same as the reported one and, therefore, we have believed that the alga of the present invention is a new species or a new variety belonging to Lobosphaera and named it as Lobosphaera TM-33. This alga has been deposited with the ATCC (Deposit No. 75630; Dec. 21, 1993). The present invention includes natural Lobosphaera TM-33 and its varieties and those belonging to the same genus having an ability of producing the trehalose exhibiting the above-mentioned properties. The varieties include those which are resulted by nature and those which are artificially prepared by known means such as irradiation with radioisotope, irradiation with ultraviolet light, chemical treatment (with, for example, nitrosoguanidine) and the like and a treatment for increasing the enzyme productivity by means of gene recombination.

(1) Morphological Properties:

When the alga was cultured on an agar medium of Bold's basal medium (hereinafter referred to as BBM) for two weeks and observed under an optical microscope, it had cup-like chloroplasts with deep cuttings. Clear pyrenoid was not found.

Figure 1:
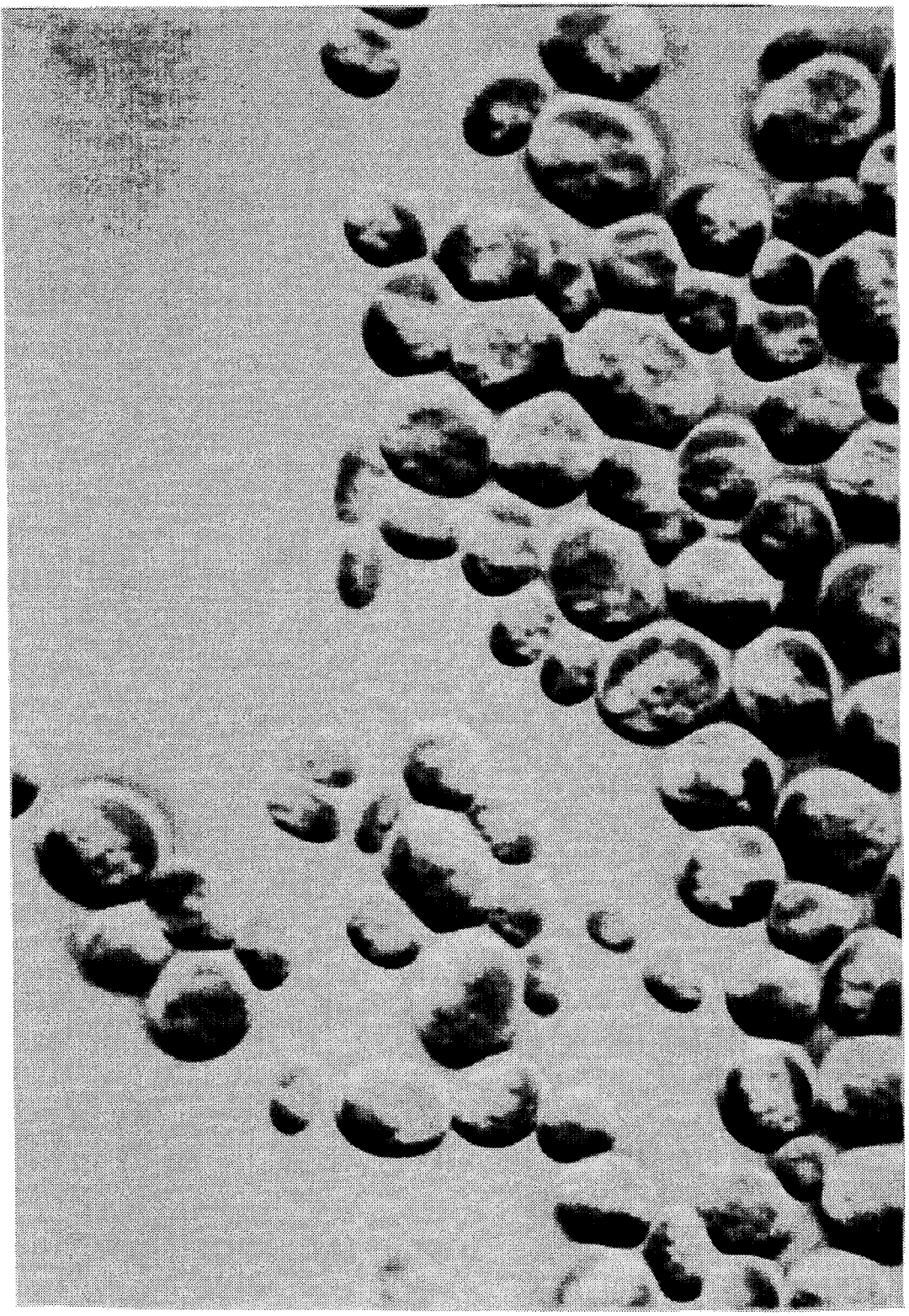
FIG. 1 is a scheme of the alga which produces trehalase of the present invention under a microscope.

(2) Properties upon Culture:

On a BBM, growth was confirmed from the fourth day. In normal agar medium, growth was confirmed after one day. FIG. 1 shows the picture of this alga under a microscope.

The alga of Lobosphaera, Chlorellaceae, Chlorophyceae, Chlorophyta producing the trehalase of the present invention grows even in homotrophical cultivation but the growing rate is higher and production of trehalase is more in heterotrophical cultivation.

1. Method of Culturing Lobosphaera TM-33

Culture of Lobosphaera TM-33 producing the trehalase of the present invention may be carried out in accordance with the following manner, though the present invention is not limited thereto.

Preferred basal medium (pH: 6.5) comprises 0.5 (w/v)% polypepton (unless otherwise stated, % is given by w/v hereinafter), 0.1% of yeast extract, 0.05% of magnesium sulfate heptahydrate, 0.05% of sodium chloride, 0.1% of monopotassium phosphate and 0.1% of dipotassium phosphate.

(1) Influence of Carbon Source

The above-mentioned basal medium containing 0.25% of various carbon sources given in Table 1 was prepared, sterilized by conventional manner and Lobosphaera TM-33 was inoculated on this medium followed by subjecting to a shake culture at 27° C. for five days in a dark chamber.

TABLE 1

| | Activity (unit/ml) | Relative Activity |
|---|---|---|
| Nothing Added | 0.78 | 24.4 |
| Glucose | 2.80 | 87.7 |
| Fructose | 2.37 | 74.2 |
| Galactose | 1.84 | 57.6 |
| Lactose | 0.79 | 24.7 |
| Sucrose | 0.69 | 21.6 |
| Trehalose | 2.81 | 88.1 |
| Glycerol | 3.19 | 100.0 |
| Cellobiose | 0.82 | 25.7 |
| Melibiose | 0.79 | 24.8 |
| Starch | 0.6 | 18.8 |

It is clear from Table 1 that this alga gives the same activity as in the case of addition of trehalose in a medium containing such as glucose, fructose, galactose, glycerol, etc. Among those, glycerol gave the best result. Preferred concentration of glycerol to be added is 0.25% to 1%.

(2) Influence of Nitrogen Source

A shake culture was carried out at 27° C. for five days using 0.25% of glycerol, 0.05% of magnesium sulfate heptahydrate, 0.05% of sodium chloride, 0.1% of monopotassium phosphate and 0.1% of dipotassium phosphate (pH: 6.5) as well as various nitrogen sources given in Table 2 and the enzymatic activity was measured. The result is given in Table 2.

TABLE 2

|  | Activity (Unit/ml) | Relative Activity |
|---|---|---|
| Ammonium Sulfate | 0.00 | 00.0 |
| Polypepton | 2.14 | 62.9 |
| Meat Extract | 1.41 | 44.0 |
| Corn Steep Liquor | 0.93 | 27.9 |
| Yeast Extract | 2.31 | 67.9 |
| 0.2% Yeast Ex + 0.2% Meat Ex | 3.20 | 100.0 |
| 0.2% Meat Ex + 1.0% Polypeptone | 1.70 | 50.0 |

It is clear from Table 2 that the use of polypepton, yeast extract, meat extract and other organic nitrogen sources gave trehalase of high activity.

The above result may give a conclusion that a medium composition with high activity comprises 1.0% of polypepton, 0.2% of yeast extract, 0.75% of glycerol, 0.05% of magnesium sulfate heptahydrate, 0.05% of sodium chloride, 0.1% of monopotassium phosphate and 0.1% of dipotassium phosphate (pH: 6.5), though the present invention is not limited thereto, however, it is possible to use other media in which the constituents which can produce the desired enzyme from the algae in large quantities by referring to the above-mentioned findings are used.

2. Method of Manufacturing Trehalase or the Product containing Trehalase

In the production of the trehalase of the present invention, Lobosphaera TM-33 is inoculated on a selected medium and cultered for two to seven days keeping the pH to 3.5–7.5 (preferably to 5–7) and the temperature at 20°–45° C. (preferably at 25°–35° C.) under shaking or aeration.

The alga which is collected from the culture broth obtained hereinabove by conventional means such as centrifugation contains the trehalase of the present invention. Examples of the products which contains the trehalase are the alga per se, or its acetone treated powders and its freeze-dried cells. It is also possible to use in the state such as a supernatant liquid prepared by subjecting the alga to disintegration by a French press, an ultrasonic wave treatment, a MANTON-GAULIN treatment, etc. followed by centrifuging; a salted-out substance obtained by adding ammonium sulfate to the supernatant liquid to an extent of 85% saturation; precipitate obtained by adding acetone, ethanol or the like to the supernatant liquid after the centrifugation; the dried powder of the precipitate; etc. If necessary, the enzyme may be further purified.

Purification of the supernatant liquid after disintegration of the cells may be carried out by a suitable combination of conventional means such as salting out, ion exchange resin treatment and the like. For example, a solid ammonium sulfate is added to the supernatant liquid after disintegrating the cells and the fractions which precipitate at the 85% saturation are collected by a centrifuger. The resulting precipitate is dissolved in 50 mM acetate buffer (pH: 5.5), placed in a dialyzing tube and well dialyzed using the buffer. Incidentally, the recovery in this salting out method by ammonium sulfate was 95%. Then, in accordance with a conventional method, ion chromatography and gel filtration are carried out using commerically available resins. With regard to the resin used for the above, at least one which is selected from TSK gel SP Toyopearl 550, TSK gel Super Q-Toyopearl 650 and TSK gel Toyopearl HW manufactured by Toso and DEAE-Sepharose CL-6B, CM-Sepharose Fast Flow, Sepharose CL-6B, Sepharose CL-4B, etc. manufactured by Farmacia may be used.

Figure 2:
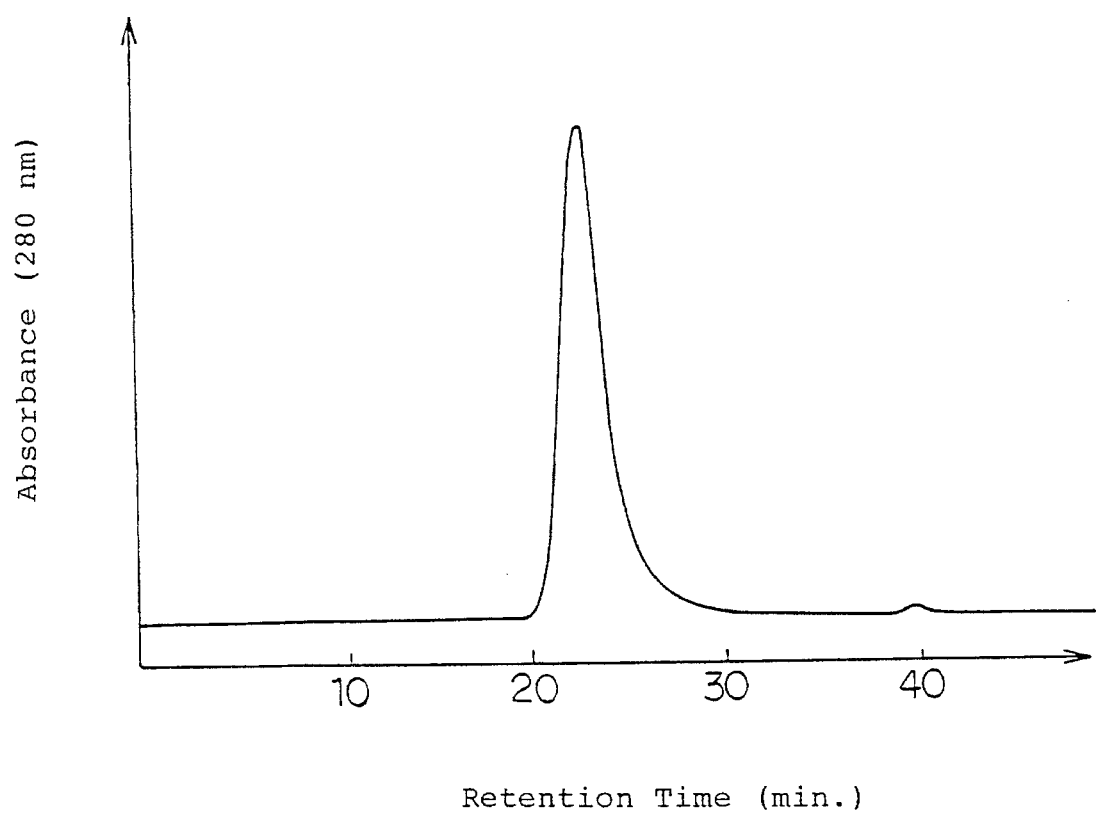
FIG. 2 is a chart when the trehalase of the present invention is subjected to an FPLC.

Finally, as shown in FIG. 2, one peak was obtained as a result of a fast protein liquid chromatography (hereinafter referred to as FPLC)(10×300 mm; 25 mM phosphate buffer [pH: 7.0], 50 mM NaCl, 0.5 ml/minute; 280 nm) by means of a gel filtration using Superose 12.

3. Properties of Trehalase

The result of the studies using the enzyme which was prepared as above will be given as follows:

(1) Method for Measuring Enzymatic Activity:

An enzyme solution (125 μl) was added to 125 μl of 0.1M trehalose solution, treated at 40° C. for ten minutes and the resulting glucose was determined by a Somogyi-Nelson method [N. Nelson: J. Biol. Chem., 153, 375 (1944)]. One unit of the enzymatic activity used here is defined as an amount of the enzyme which produces the reducing sugar corresponding to 2 μmole of glucose per minute.

(2) Action (a) When it is made acted on a diluted aqueous solution of trehalose, it hydrolyzes trehalose into glucose.

(b) When the enzyme is made acted on glucose of high concentration (e.g. 50% w/v), it synthesizes trehalose in a yield of 5–20% [the yield= (trehalose concentration)/(initial glucose concentration)].

(3) Substrate Specificity

This enzyme is with very high specificity and, while it hydrolyzes trehalose, 2-deoxytrehalose and 2,2'-dideoxytrehalose, it does not hydrolyze methyl-α-glucoside, phenyl-α-glucoside, maltose, isomaltose, sucrose, lactose, cellobiose soluble starch, etc.

(4) Optimum pH and Stability against pH

Figure 3:
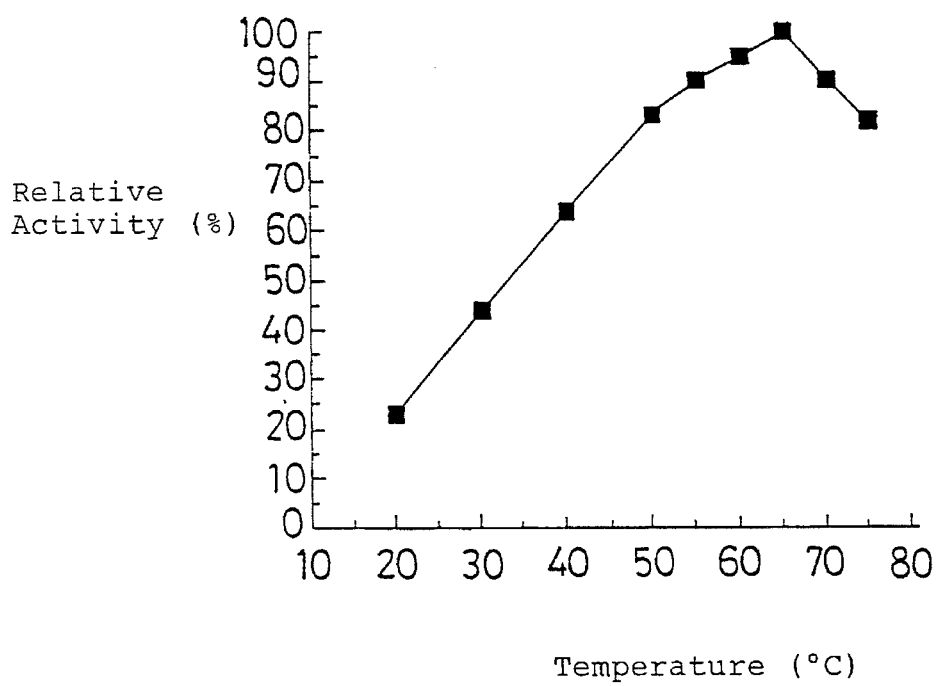
FIG. 3 is a graph showing the optimum temperature of trehalase of the present invention.
Figure 4:
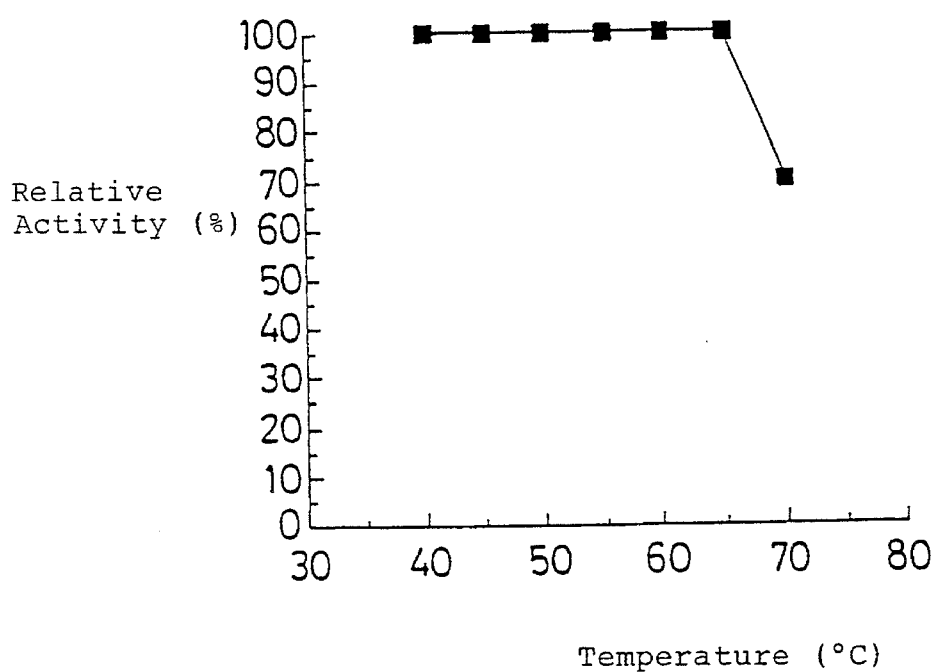
FIG. 4 is a graph showing the stability of trehalase of the present invention against temperature.

Activity of the enzyme at various pH was measured by the above-mentioned method for measuring the enzymatic activity and the optimum pH was determined. The result is given in FIG. 3 which shows the optimum pH of this enzyme is 5–6. Further, the residual activity after keeping at 5° C. for 20 hours at various pH was measured and the reuslt is that, as shown in FIG. 4, the activity does not change until pH 9 and, even at pH 10, it exhibits a residual activity of 83%.

(5) Optimum Temperature and Stability against Temperature

Figure 5:
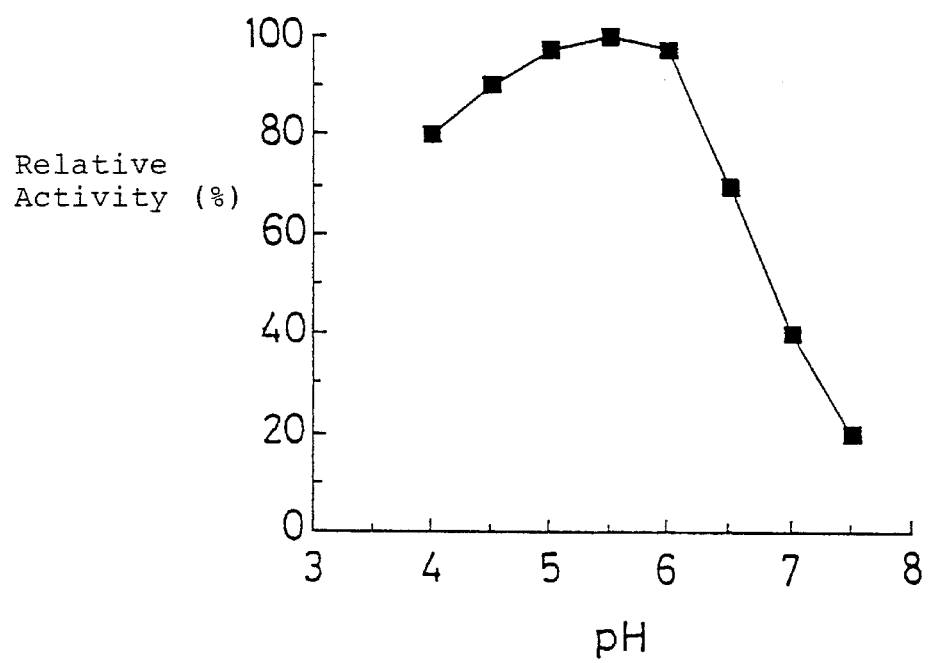
FIG. 5 is a graph showing the optimum pH of trehalase of the present invention.
Figure 6:
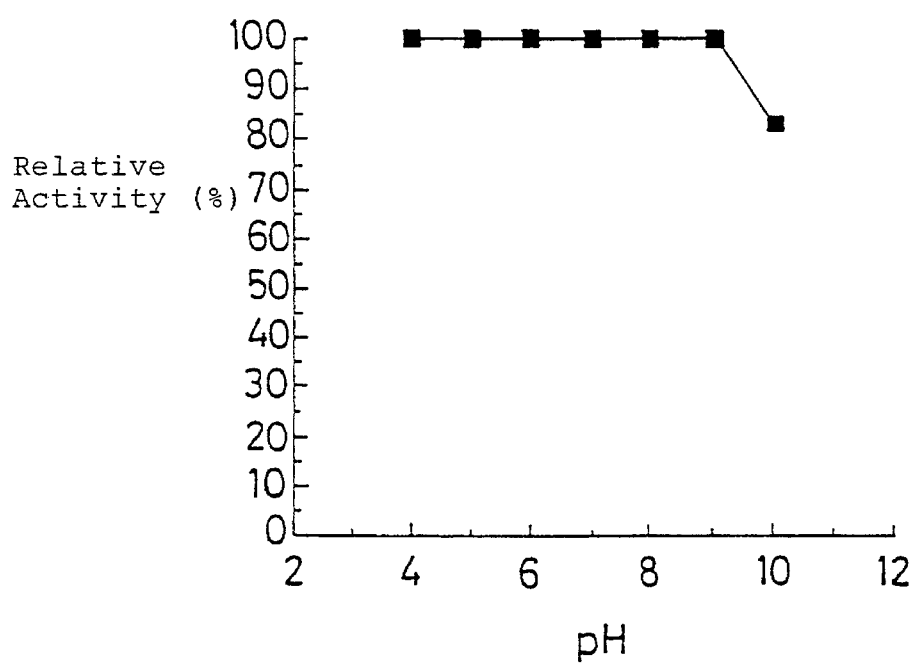
FIG. 6 is a graph showing the stability of trehalase of the present invention against pH.

Activity at various temperatures was measured by means of the above-mentioned method for measuring the enzymatic activity and the optimum temperature was determined. The result is given in FIG. 5 wherefrom the optimum temperature of this enzyme is 65° C. In the meanwhile, the residual activity after keeping at pH 5.5 for ten minutes at various temperatures was measured and, it was found that, as shown in FIG. 6, the activity did not change up to 65° C. and, even at 70° C., about 70% of residual activity was noted.

(6) Molecular Weight

The molecular weight of this enzyme was determined by means of a gel filtration of FPLC using a column of Superose 12 and was found to be 400,000 to 500,000. The subunit molecular weight as measured by an SDS-PAGE method was 180,000–250,000.

(7) Isoelectric Point

The isoelectric point as measured by a method of Vesterberg and Svensson (Acta Chem. Scand., (1966) 20, 820) using a column (110 ml) of Amphorite (Farmacia) (pH: 3.5–10.0) was 2.7.

(8) Staining of carbohydrates in the enzyme protein

This enzyme is a glycoprotein since the enzyme is positive to a staining according to a method by R. M. Zacharrius, et al. (Anal. Biochem., (1960) 30, 148).

(9) Inhibition and Activation

Various salts and reagents were kept at 30° C. for one hour at the concentration of 2.5 mM and made to react with this enzyme to measure the activity. The result was that, as compared with the control, the enzymatic activity was inhibited to an extent of 88% by trivalent iron ion and to an extent of 50% or more by 2.5 mM aluminum ion while it was not inhibited by a divalent lead ion and sodium ethylenediaminetetraacetate (EDTA).

It was further found that magnesium and calcium ion had no effect of increasing the stability of this enzyme.

4. Method of Manufacturing Trehalose by Trehalase

The trehalase of the present invention acts on trehalose and hydrolyzes it into glucose and, at the same time, it produces trehalose in reversed manner in the presence of glucose of high concentration. Thus, when a treatment is carried out by adding trehalase to a glucose solution, a condensation reaction takes place whereby trehalose is produced in a single step in high yield in economical way starting from glucose which is available in low cost. As hereunder, further illustration will be made by referring to specific examples.

The concentration of glucose used is 5–80% (w/w) or, preferably, 40–60% (w/w). The temperature during the reaction is 20°–80° C. or, preferably, 40°–70° C. Preferred pH is within a range of 4 to 8. The necessary unit numbers of the enzyme is 0.1–200 units per gram of glucose. Though the reaction time varies depending upon the amount the enzyme used, it is selected from the range of 0.1 to 100 hours. As a result of such a simple operation, it is possible to afford trehalose in a yield of 10–20% [yield= (trehalose concentration)/(initial glucose concentration)]. It is not necessary that the enzyme used there is particularly purified but the algae per se, freeze-dried algae, acetone powder of the algae or a crude enzyme solution will do so far as it contains the trehalase. In addition, immobilized enzyme may be used as well. In the case of the immobilized enzyme, ion exchange resin or porous ceramic may be used as an immobilizing material and, for the immobilization, a crosslinking agent such as glutaraldehyde may be used.

The reaction solution which is subjected to the above-mentioned treatment contains trehalose, the unreacted glucose, etc. Though the reaction solution per se, the reaction solution which is concentrated or is evaporated to dryness and a powder prepared by drying the reaction solution may be used as a material containing trehalose, the reaction solution may further be highly purified by one of the common means selected from ion exchange resin treatment, activated charcoal chromatography, chromatographic operations using adsorbing resin, etc., recrystallization and the like or a combination thereof.

5. Method of Manufacturing 2,2'-Dideoxytrehalose and 2-Deoxytrehalose

The same method as in the manufacture of trehalose from glucose using the trehalase of the present invention may be used whereby 2,2'-dideoxytrehalose can be manufactured from 2-deoxyglucose.

An example will be that the concentration of 2-deoxyglucose is 20–80% (w/w) or, preferably, 50–70% and the temperature is 20°–80° C. or, preferably, 40°–60° C. The reaction may be carried out at the pH of within a range of 4–8. The necessary unit numbers of the enzyme in this case are 0.1–200 units per gram of 2-deoxyglucose. Though the reaction time may vary depending upon the amount of the enzyme used, it is selected from a range of 0.1 to 100 hours. As a result of such a simple operation, it is possible to afford 2,2'-dideoxytrehalose in a yield of 20–50% [yield= (concentration of 2,2'-dideoxytrehalose)/(initial concentration of 2-deoxyglucose)].

Further, 2-deoxytrehalose may be prepared from a mixture of 2-deoxyglucose and glucose in a molar ratio of 10:1 to 1:1 (preferably from 5:2 to 10:1; the sugar concentration as a mixture is 10–80% (w/w) or, preferably, 50–70% (w/w)) at the temperature of 20°–80° C. (preferably 40°–60° C.) at the pH of within a range of 4 to 8. The unit of the enzyme necessary therefor may be 0.1–200 units per gram of 2-deoxyglucose. Though the reaction time may vary depending upon the amount of the enzyme used, it is selected from the range of 0.1 to 100 hours. As a result of such a simple opertion, it is possible to afford 2-deoxytrehalose in a yield of 10–30% [yield=(concentration of 2-deoxytrehalose)/(initial concentrations of 2-deoxyglucose and glucose)].

The substance which was produced as a result of the present reaction may be purified by known methods and its structure may be confirmed by an instrumental analysis. For example, the reaction product is made into a single substance by means of an activated charcoal column chromatography, gel filtration and recrystallization and then subjected to a molecular weight measurement by a fast atom bombardment mass (hereinafter referred to as Fab-MS) and a struture analysis by a $^{13}C$ nuclear magnetic resonance (NMR).

Novel trehalase of the present invention and the method of manufacturing the same will be given as hereunder:

EXAMPLE 1

Lobosphaera TM-33 was inoculated on a nutrient agar slant medium, cultured at 27° C. for five days, one loopful of it was inoculated on 500 ml of a liquid medium (pH: 6.5) comprising 0.2% of yeast extract, 1.0% of polypepton, 0.25% of glycerol, 0.05% of magnesium sulfate heptahydrate, 0.1% of dipotassim phosphate and 0.1% of potassium dihydrogen phosphahte and subjected to a shake culture in a dark chamber at 27° C. for five days with aeration. After the cultivation, the enzymatic activity was measured and found to be about 3 units of trehalase per ml of the broth. The culture broth was centrifuged to collect the algae, defatted by adding 200 ml of acetone thereto and dried to give 0.15 g of acetone powder of the algae. Each mg of the powder exhibited 10 units of enzymatic activity.

EXAMPLE 2

Lobosphaera TM-33 strain was inoculated on a nutrient agar slant, cultured at 27° C. for five days, one platinum loopful of the algae was inoculated on 500 ml of a liquid medium (pH: 6.5) comprising 0.2% of yeast extract, 1.0% of polypepton, 0.25% of glycerol, 0.05% of magnesium sulfate heptahydrate, 0.1% of dipotassium phosphate and 0.1% of potassium dihydrogen phosphate and shake-cultured at 27°

C. for five days in a dark chamber with aeration. After the cultivation, enzymatic activity was measured and found to be 3 units of trehalase per ml of the broth. After the shake culture, the culture broth was centrifuged to collect the algae, the algae was disintegrated by means of a French press (1,500 Kgf/cm$^2$) and salted out with 90% saturated ammonium sulfate at room temperature. After that, the salted out product was dissolved in 50 mM acetate buffer (pH: 5.5) and dialyzed in 50 mM acetate buffer using an acetate dialyzing tube to give 10 ml of a solution containing trehalase. The resulting enzyme solution contained 140 units of trehalase per ml.

EXAMPLE 3

Glucose (5 kg) was dissolved in 3 liters of water and the solution was adjusted to pH 5.5 by adding citric acid thereto. To this solution was added the enzyme solution prepared in Example 1 in an amount of 50 units per gram of glucose and the mixture was stirred at 50° C. for 12 hours. The reaction solution was analyzed by means of a high performance liquid chromatography (hereinafter referred to as HPLC; column: Amido-80 manufactured by Toso; solvent: acetonitrile/water 70% (v/v); flow rate: 1.0 ml/min; temperature: 35° C.; pump: CCPD of Toso; detector: RI-8012 of Toso) and found to contain 20% (w/w) of trehalose.

The reaction solution was further heated at 90° C. for ten minutes to inactivate the enzyme and subjected to an activated charcoal column chromatogrphy (10×150 cm) whereupon trehalose was adsorbed with the column. Then the column was washed with 60 liters of distilled water to remove glucose and eluted with 20 liters of 10% ethanol to give trehalose. The ethanolic fraction was concentrated to give 0.3 kg of trehalose of 97% purity.

EXAMPLE 4

Glucose (5 kg) was dissolved in 4 liters of water and citric acid was added thereto to adjust to pH 5.5. To this solution was added the enzyme solution obtained in Example 2 in an amount of 50 units per gram of glucose and the mixture was made to react at the same temperature for 12 hours and analyzed by the same HPLC conditions as in Example 3 whereupon it contained 20% (w/v) of trehalose.

The reaction solution was heated at 90° C. for ten minutes to inactivate the enzyme and subjected to an activated charcoal column chromatography (10×150 cm) whereupon trehalose was adsorbed with the column of activated charcoal. Then the column was washed with 40 liters of pure water to remove the unreacted glucose and eluted with 20 liters of 10% ethanol to elute trehalose. The eluted fraction was concentrated to give 0.8 kg of trehalose of 95% purity.

EXAMPLE 5

A carrier for preparing an immobilized enzyme (1 kg; VA-20 which was an anionic exchange resin manufactured by Mitsubishi Kasei) was dipped in 50 mM acetate buffer, well deaerated, the enzyme solution (200,000 units) prepared by a method of Example 2 was added and the mixture was allowed to stand overnight to immobilize the enzyme with the carrier. The carrier in which the enzyme was immobilized was washed with an acetate buffer, filled in a column (6×50 cm) while water of constant temperature was circulated in a column jacket to make the column temperature 50° C. Then a column (10×100 cm) filled with an activated charcoal was connected after the immobilized enzyme column and 30% glucose (3 kg glucose/10.0 liters distilled water; w/w) was circulated into the the inactivated charcoal column at the rate of SV 2 (SV: the amount of the liquid per hour/adsorbent). As a result, trehalose was accumulated in the activated charcoal column and, when the activated charcoal column was washed with 10% (w/v) ethanol, trehalose was eluted. When the 10% ethanolic fraction was concentrated, 1 kg of trehalose of 95% purity was obtained.

EXAMPLE 6

Figure 7:
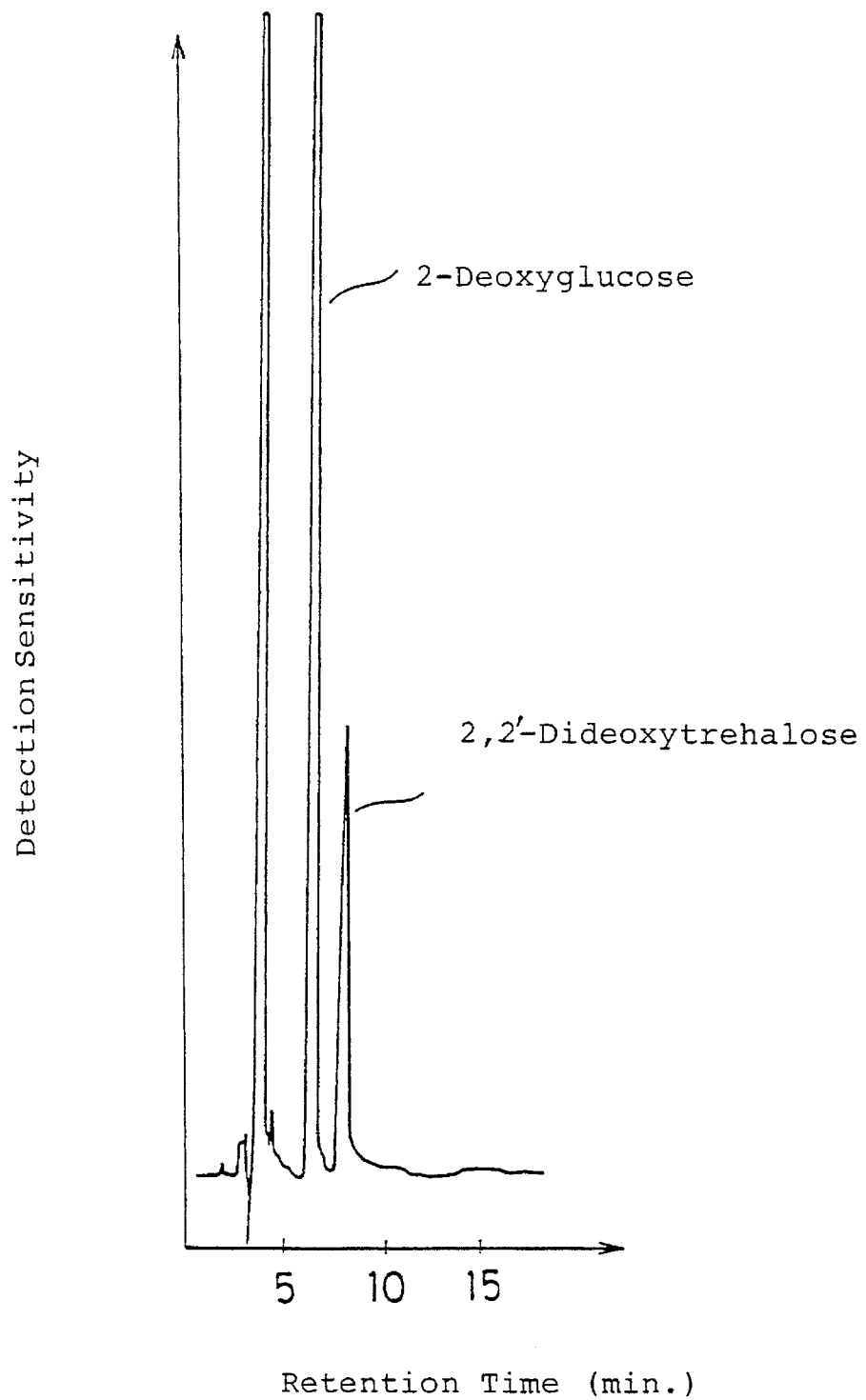
FIG. 7 is an HPLC chart of 2,2'-dideoxytrehalose produced when 2-deoxyglucose is treated with trehalase.

2-Deoxyglucose (1.4 g) was dissolved in 0.6 ml of 50 mM acetate buffer (pH: 5.5), 50 ml of the enzyme solution prepared in Example 1 was added and the mixture was made to react at 70° C. for 48 hours. After the enzyme was inactivated by heating at 100° C. for five minutes, a part of the reaction solution was analyzed by a high performance liquid chromatography under the same conditions as in Example 3. The result is given in FIG. 7.

Figure 8:
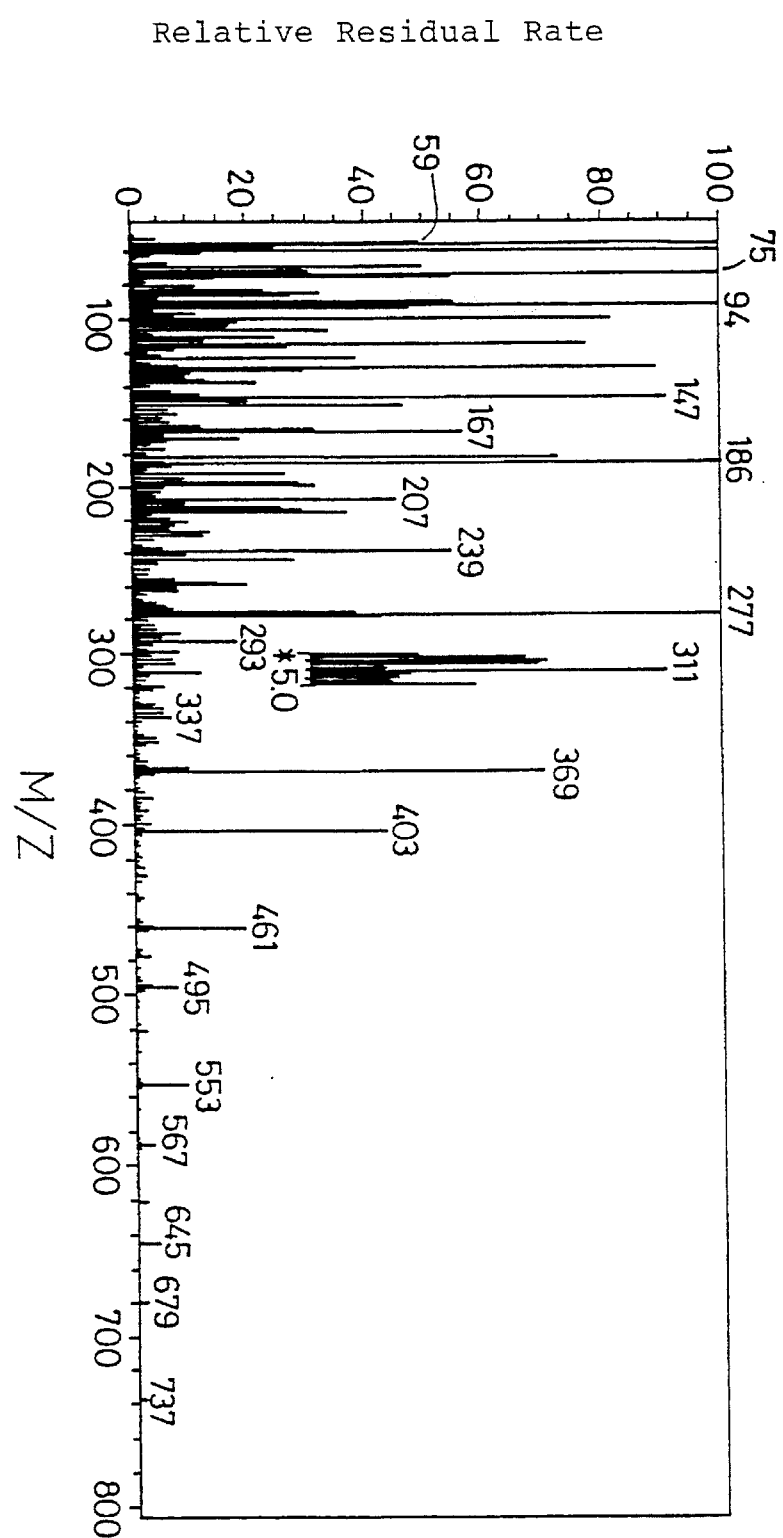
FIG. 8 is an Fab-MS analysis spectrum of the condensation product shown in Example 6 of the present invention.
Figure 9:
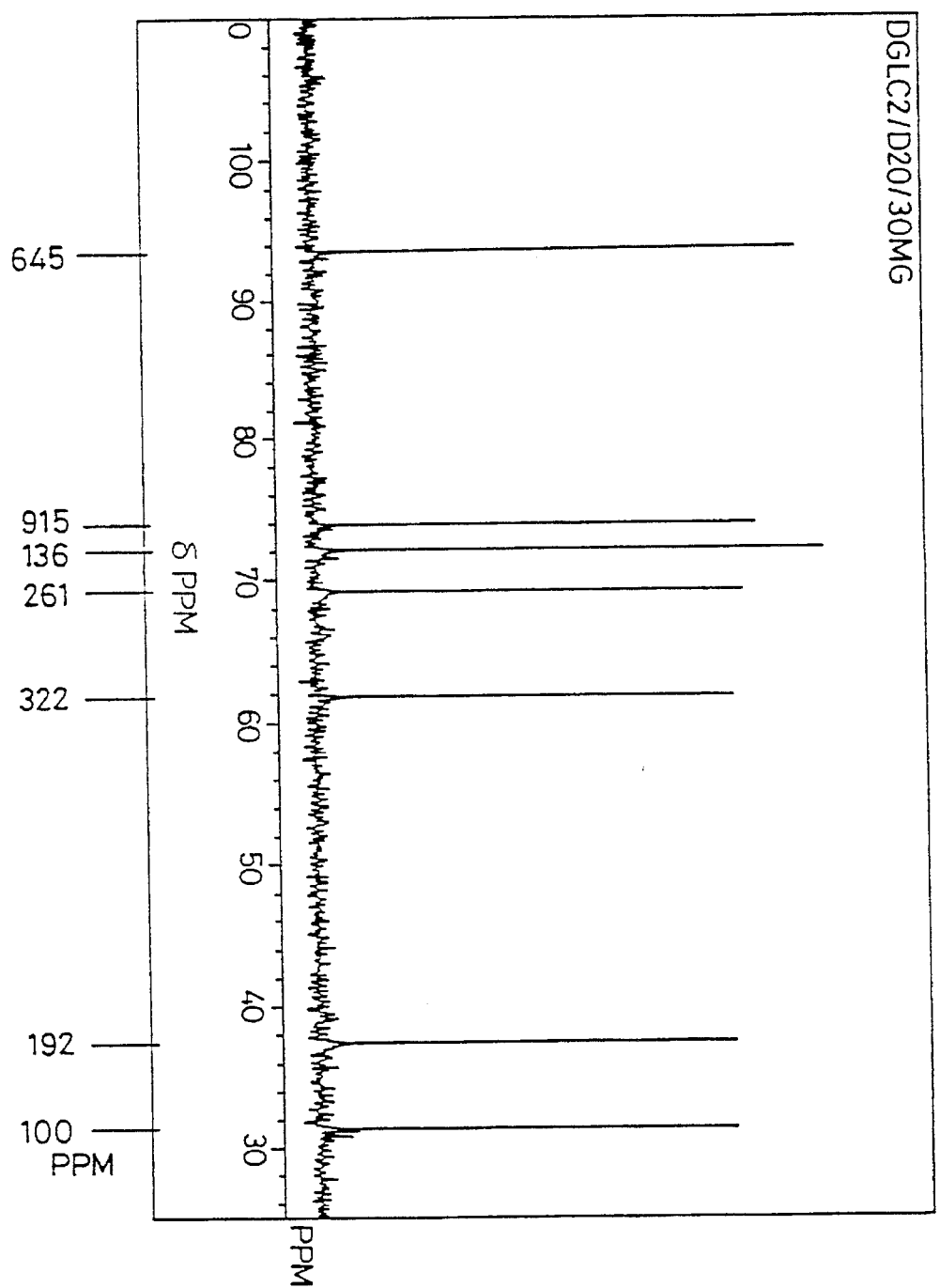
FIG. 9 is a $^{13}$C-NMR analysis of the condensation product in Example 6 of the present invention.
Figure 10:
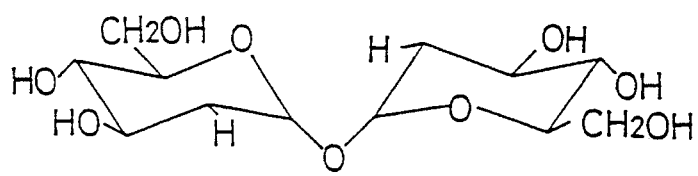
FIG. 10 is a structural formula of 2,2'-dideoxytrehalose.

After completion of the reaction, the solution diluted with 6 ml of distilled water was subjected to a treatment with an activated charcoal column (2×11 cm) and Bio gel P-2 (2.5×143 cm) of Biorad to give 162 mg of 2,2'-dideoxytrehalose of 99% purity. As shown in FIG. 8, molecular weight of the resulting compound was measured by means of mass spetrum (Fab-MS) (instrument: JEOL JMX-DX303H mass spectrometer; matrix: glycerol) and, as a result of $^{13}$C nuclear magnetic resonance (NMR) (instrument: JEOL JMX-EX207 68.8 MHz; internal standard: acetone (δ31.4 ppm) and optical rotation (+153.80)), the structure of 2,2'-dideoxytrehalose as shown in FIG. 10 was confirmed.

EXAMPLE 7

Figure 11:
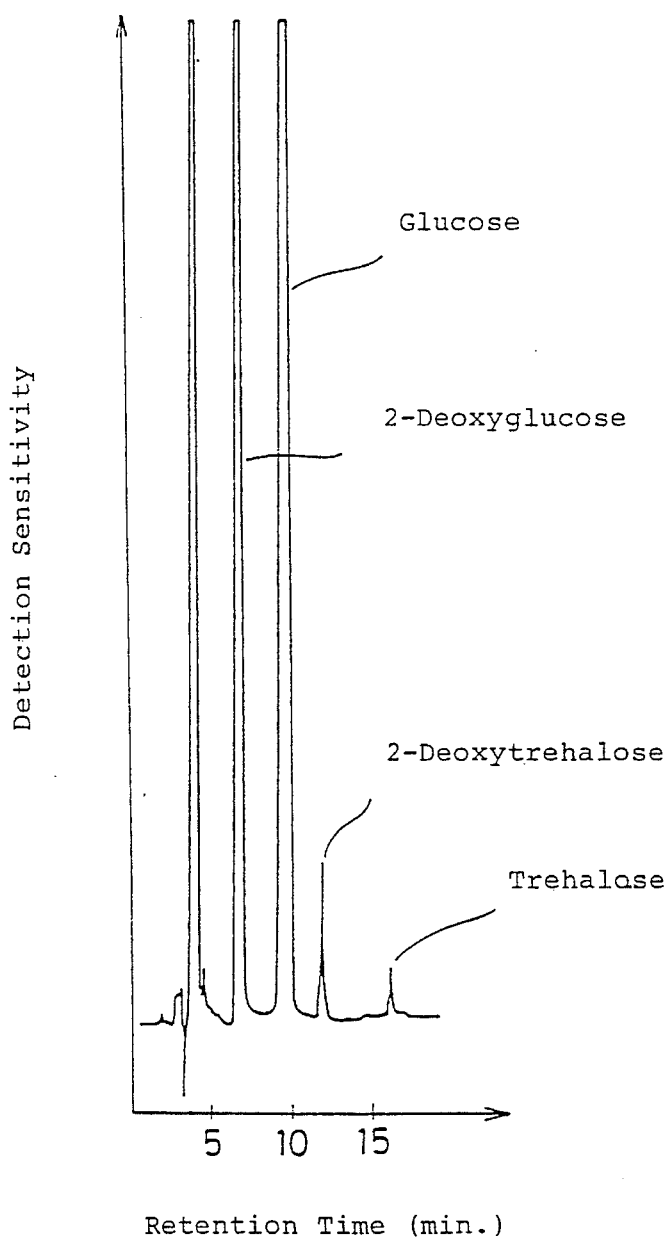
FIG. 11 is an HPLC chart of 2-deoxytrehalose produced by the reaction of 2-deoxyglucose and glucose with trehalase.

2-Deoxyglucose (500 mg) and 200 mg of glucose were dissolved in 1 ml of 50 mM acetate buffer (pH: 5.5), 50 units of trehalase produced by Lobosphaeraceae was added and made to react at 70° C. for 48 hours. A part of the reaction solution was analyzed by means of a high performance liquid chromatography under the same conditions as in Example 3. The result is given in FIG. 11.

Figure 12:
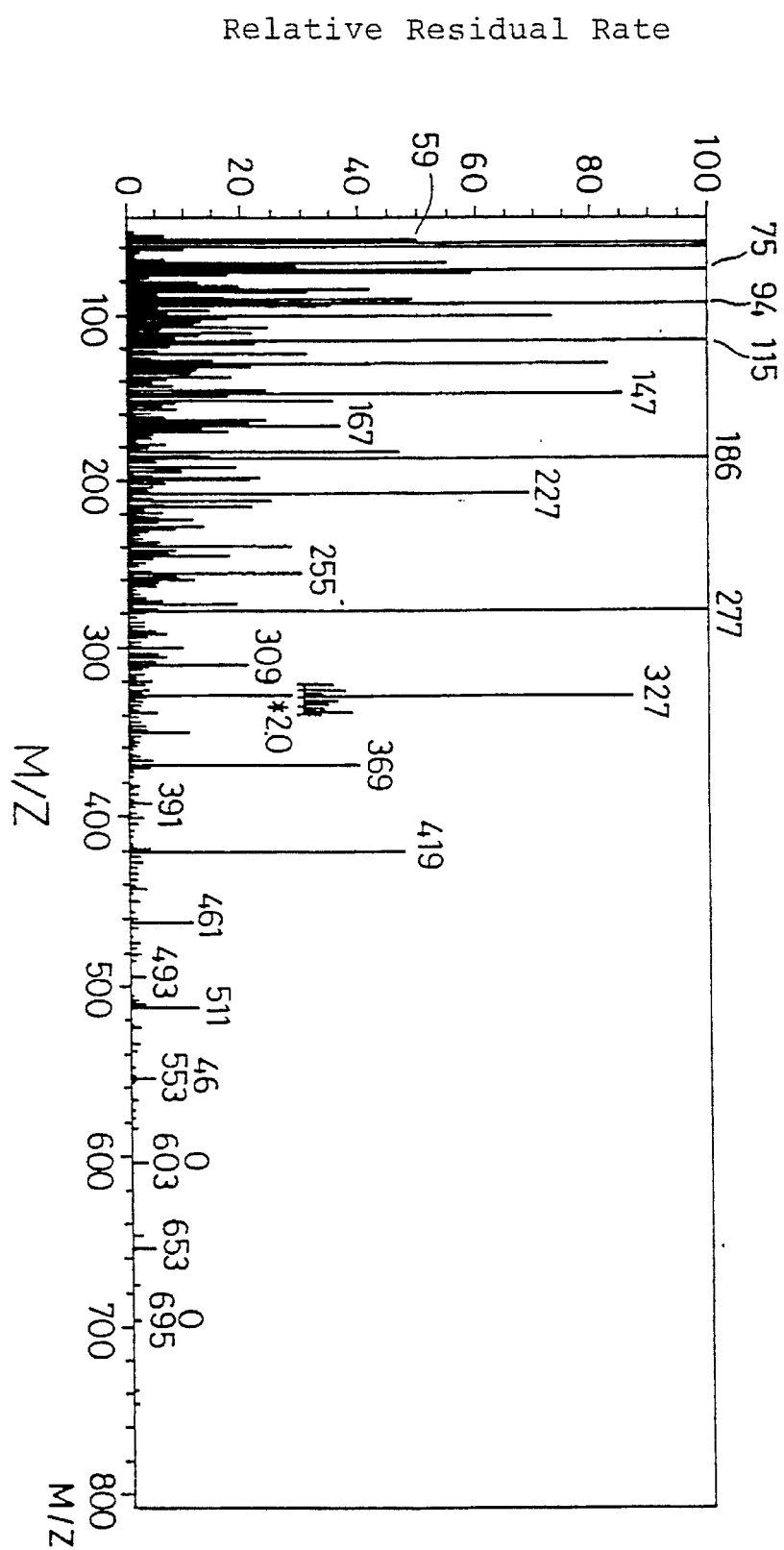
FIG. 12 is an Fab-MS analysis spectrum of the condensation product in Example 7 of the present invention.
Figure 13:
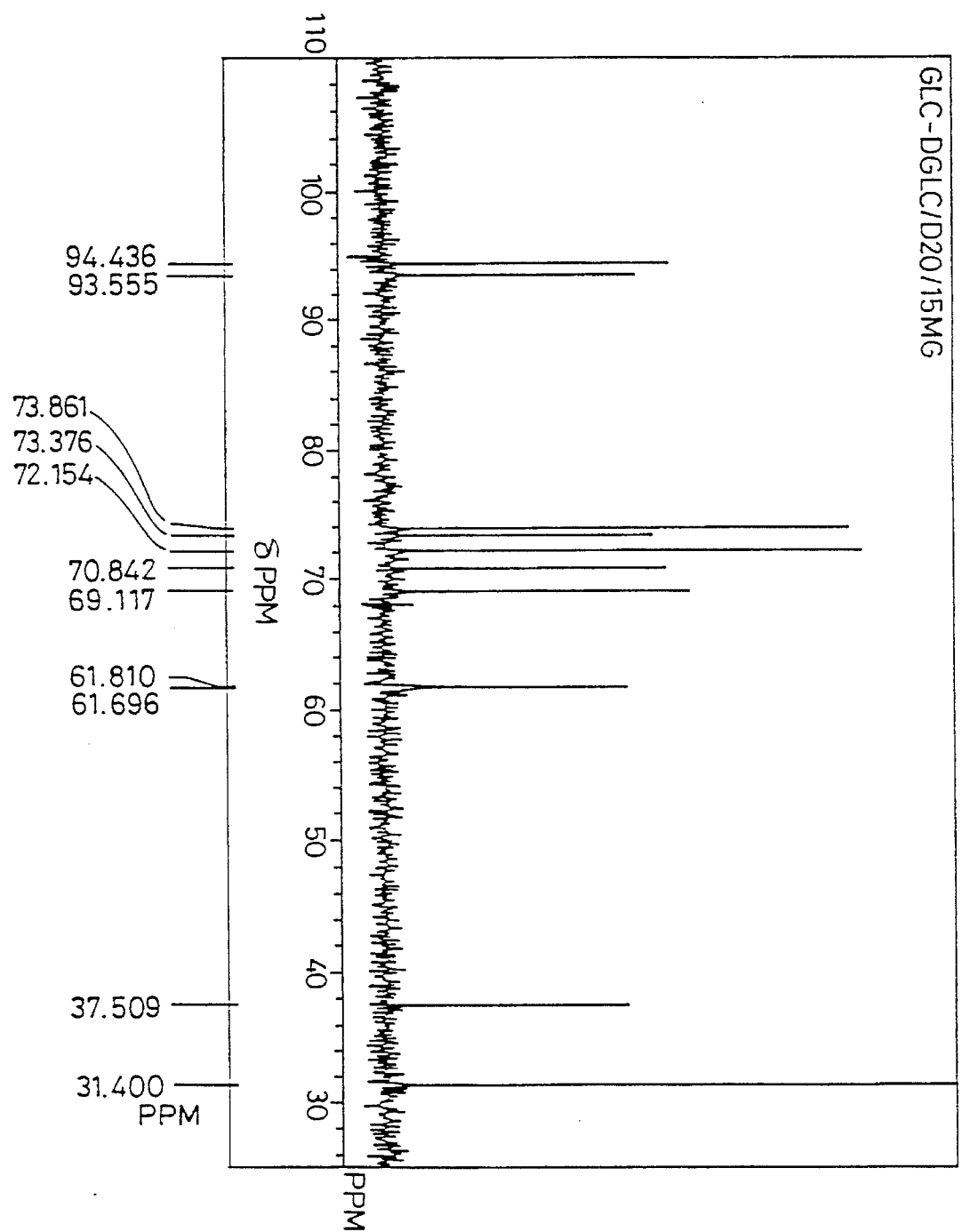
FIG. 13 is a $^{13}$C-NMR analysis of the condensation product in Example 7 of the present invention.
Figure 14:
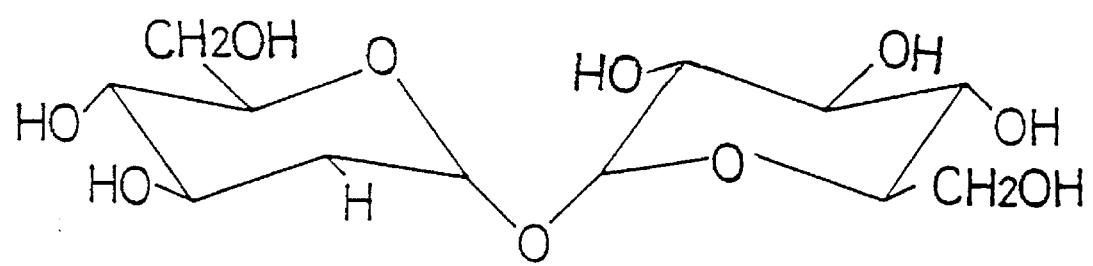
FIG. 14 is a structural formula of 2-deoxytrehalose.

After completion of the reaction, the mixture was treated at 100° C. for 5 minutes to inactivate the enzyme, diluted with 6 ml of distilled water and subjected to a treatment with an activated charcoal column (2×11 cm) and a gel filtration using Bio gel P-2 (2.5×143 cm) to give 40 mg of 2-deoxytrehalose of 99% purity. Molecular weight of the resulting compound was measured by a mass spectrum (Fab-MS) as shown in FIG. 12 and the structure of 2-deoxytrehalose as shown in FIG. 14 was confirmed by measuring $^{13}$C nuclear magnetic resonance (NMR) as shown in FIG. 13 and optical rotation (+165.20°).

Both substances given in Examples 6 and 7 were reported already though no synthetic method thereof using trehalase has been known yet. When trehalase of the present invention is used, production of trehalose from glucose; that of 2,2'-dideoxytrehalose from 2-deoxyglucose; and that of 2-deoxytrehalose from a mixture of 2-deoxyglucose and glucose are resulted in high yield. In addition, no complicated purification is needed whereby the product of high purity can be manufactured in low cost.

EXPERIMENTAL EXAMPLE 1

Trehalase of the present invention was purified to a single substance by means of FPLC and 45 µl of the resulting trehalase (trehalase enzyme concentration: 1 mg/ml; 50 mM Tris hydrochloric acid buffer (pH: 8.6)) was denatured by heating at 100° C. for 20 minutes. After that, 5 μl of glycopeptidase F (0.5 unit/ml; Takara Shuzo) was added to the thermally denatured trehalase and made to react at 37° C. for 12 hours to remove sugars. After that, molecular weight of 50,000–60,000 was confirmed by an SDS-PAGE of acryl amide gradient gel (Multiplate gel 4/15; manufactured by Daiichi Kayaku) while that of about 100,000–120,000. was confirmed by NATIVE-PAGE measurement. The trehalase which was not treated with glycopeptidase F, i.e. the control, was confirmed to be with a molecular weight of 180,000–250,000 as a result of SDS-PAGE and was dyed in red by staining of carbohydrates in the enzyme protein.

When trehalose is manufactured using the novel trehalase of the present invention, there are advantages, as compared with a method of extracting living cells or the culture broth, that (1) trehalose can be direclty manufactured from glucose and, therefore, the reaction is simple giving no by-product whereby the product can be safely used as food and (2) trehalose can be produced in high yield in which the starting material other than the enzyme is glucose only whereby the cost becomes very low.

Further, trehalose has preventing actions against undesired effects caused by freezing and drying and an anticaries action. Moreover, it is useful as a sweetening agent in food manufacturing area and its use is very broad such as freeze storing of enzyme, etc. Furthermore, in the area of pharmaceuticals, trehalose derivatives have been utilized as anticancer drugs, etc. and, therefore, its practical applications can be expected.

In addition, with regard to the manufacture of 2,2'-dideoxytrehalose and 2-deoxytrehalose, they can be directly manufactured from 2-deoxyglucose and a mixture of 2-deoxyglucose and glucose, respectively, as compared with a method by chemical synthesis. Accordingly, the purifying step is simple and industrial utilization thereof is now possible.

Consequently, trehalase and the method of manufacturing trehalose using the enzyme are quite useful in industry.

We claim:

1. A substantially biologically pure culture of an alga species Lobosphaera TM-33 deposited as ATCC 75630.

* * * * *